United States Patent [19]

Utterberg

[11] Patent Number: 5,071,413
[45] Date of Patent: Dec. 10, 1991

[54] UNIVERSAL CONNECTOR

[76] Inventor: David S. Utterberg, 1080 Chestnut St., San Francisco, Calif. 94109

[21] Appl. No.: 538,236

[22] Filed: Jun. 13, 1990

[51] Int. Cl.$^5$ .......................................... A61M 25/00
[52] U.S. Cl. .................................... 604/283; 604/411; 604/415; 604/905
[58] Field of Search ............... 604/280, 283, 284, 264, 604/272, 273, 411–415, 905

[56] References Cited

U.S. PATENT DOCUMENTS

| | | |
|---|---|---|
| 3,940,003 | 2/1976 | Larson . |
| 4,058,121 | 11/1977 | Choksi et al. . |
| 4,369,781 | 1/1983 | Gilson et al. . |
| 4,452,473 | 6/1984 | Ruschke . |
| 4,511,359 | 4/1985 | Vaillancourt . |
| 4,559,043 | 12/1985 | Whitehouse et al. . |
| 4,588,403 | 5/1986 | Weiss et al. ................... 604/411 |
| 4,601,703 | 7/1986 | Herlitze ................... 604/415 X |
| 4,610,374 | 9/1986 | Buehler . |
| 4,610,469 | 9/1986 | Wolff-Mooij . |
| 4,629,455 | 12/1986 | Kanno . |
| 4,636,204 | 1/1987 | Christopherson et al. . |
| 4,673,400 | 6/1987 | Martin . |
| 4,710,180 | 12/1987 | Johnson . |
| 4,790,830 | 12/1988 | Hamacher . |
| 4,834,152 | 5/1989 | Howson et al. . |
| 4,981,469 | 1/1991 | Whitehouse et al. ........... 604/905 X |
| 4,998,713 | 3/1991 | Vaillancourt ................... 604/283 |
| 4,998,927 | 3/1991 | Vaillancourt ................... 604/283 |

Primary Examiner—John D. Yasko
Attorney, Agent, or Firm—Garrettson Ellis

[57] ABSTRACT

A universal connector is described, being capable of both connection with female luer connectors and penetration of resealable-diaphragm connection sites. The connector comprises a tubular member defining a first tubular section having a distal end capable of resealably penetrating a latex resealable-diaphragm injection site. Aperture means are provided adjacent the distal end of the tubular member for communication with the lumen of the tubular member with the exterior. The tubular member also defines a frustoconical male luer section positioned proximally of the first tubular section and proportioned to be sealable with female luer connectors. The male luer section has a minimum diameter that is greater than the maximum diameter of the first tubular section. Annular step means are provided separating the first tubular section and male luer section, and means are provided, spaced proximally of the frustoconical male luer section, for providing connection with a fluid conduit.

27 Claims, 3 Drawing Sheets

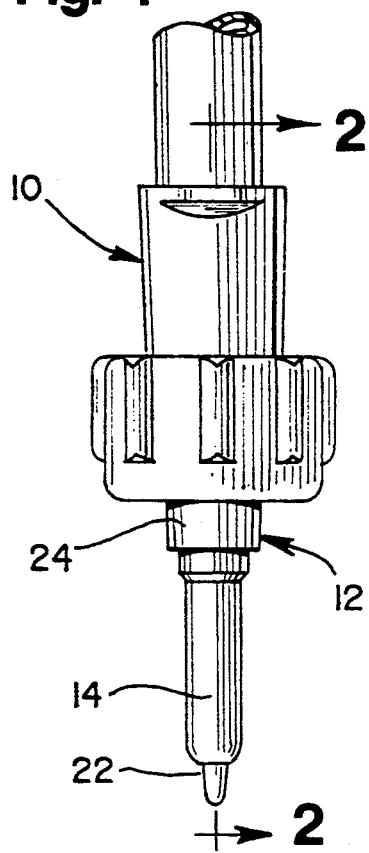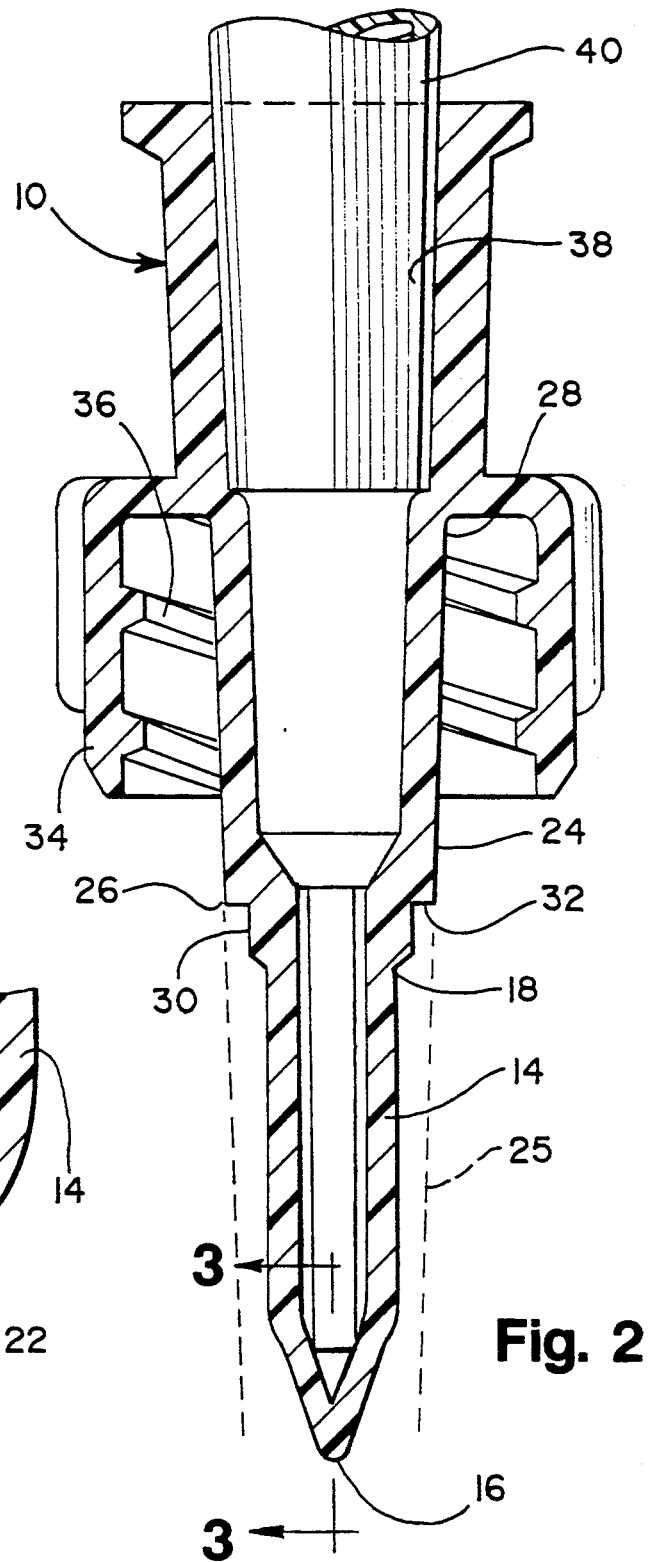

Fig. 4A
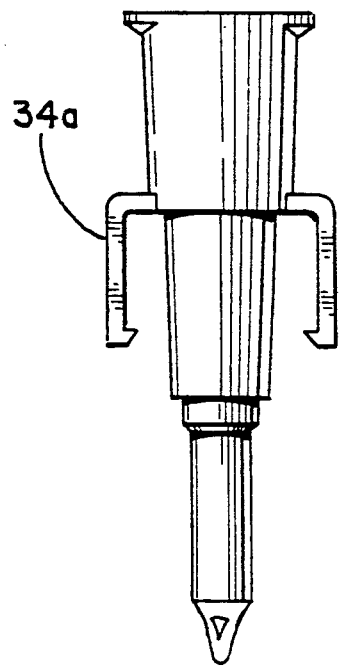
Fig. 4B
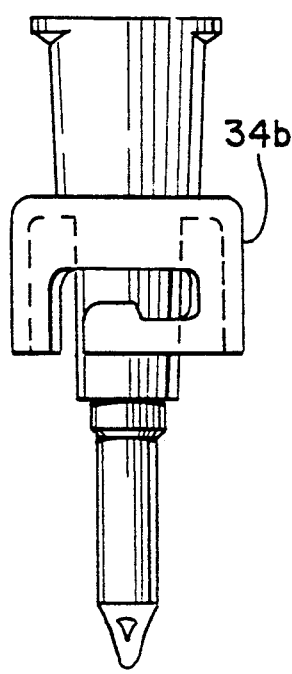
Fig. 4C
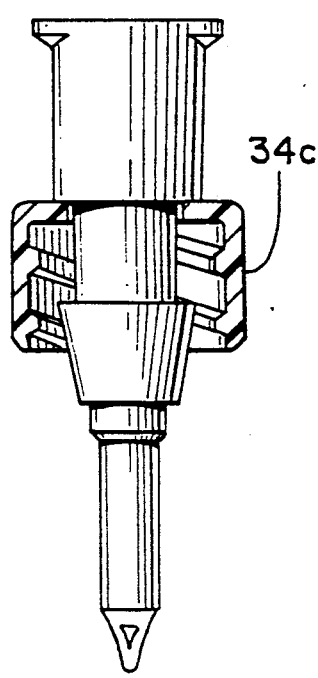
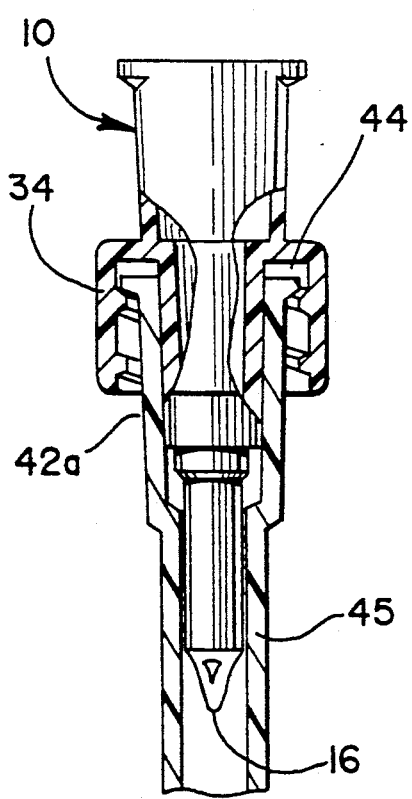
Fig. 5A
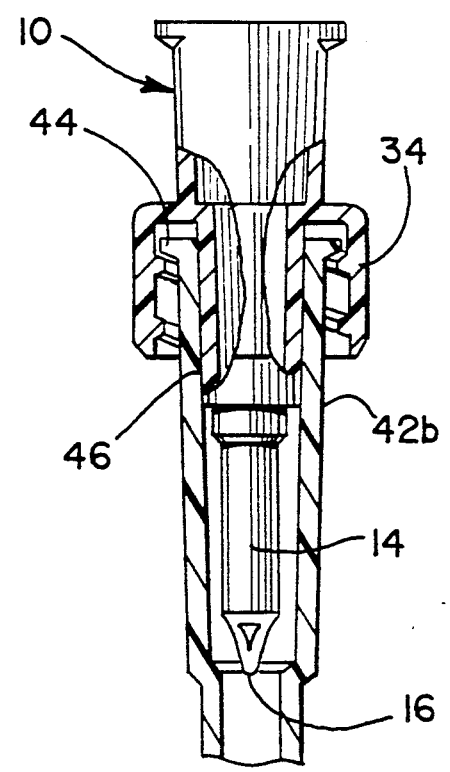
Fig. 5B

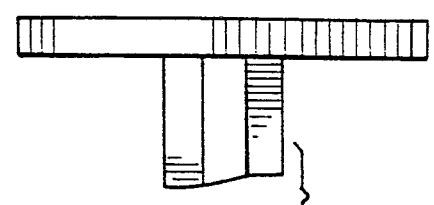
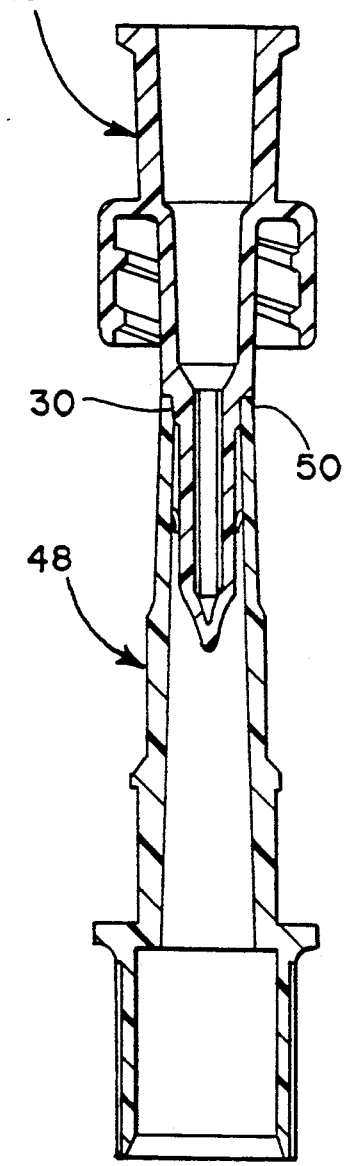
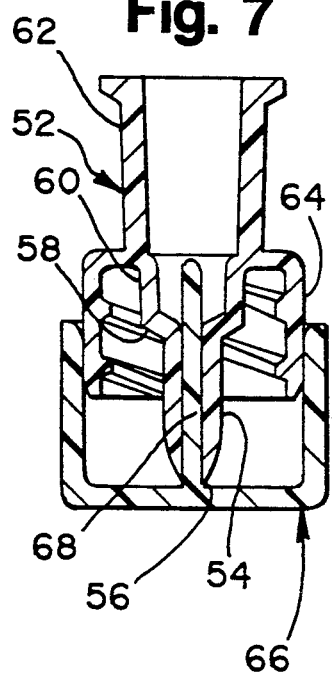
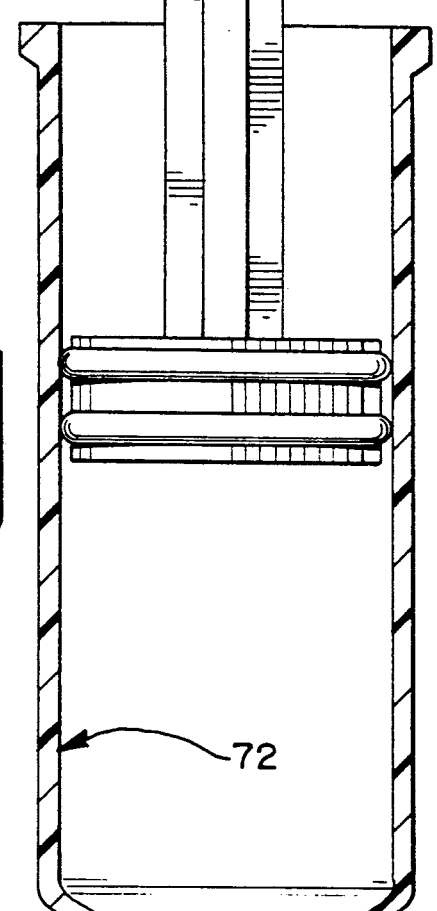
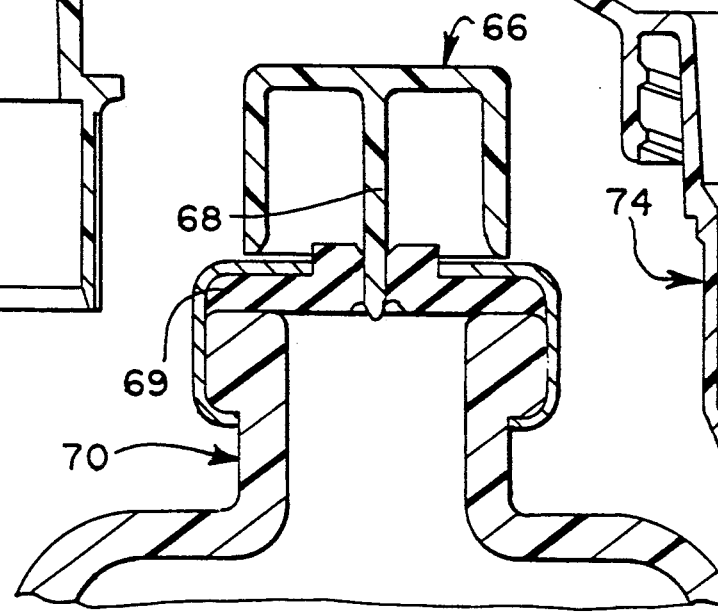

UNIVERSAL CONNECTOR

BACKGROUND OF THE INVENTION

There is a need in the medical field and elsewhere to make safe, substantially aseptic connections between fluid conduits. For example, dialysis blood flow sets require many of such connections in the set-up of a dialysis procedure. Parenteral solution administration sets, blood administration sets, and many similar medical devices have the same requirement. Also, syringes need to penetrate into vials of medication or the like in such a substantially aseptic manner.

As a technical problem, a specific medical device such as a component for connection to a medical set may have a connector of a particular design. Then, with the onset of a medical emergency or other circumstance, it may be necessary to immediately change the medical procedure, which may involve a change of connection on the part of the component. However, in many circumstances, the new medical component to which the connection is to be made may have a connection site that is incompatible with the component connector at hand. In such a circumstance, a new component must be obtained and put into use, all of which can waste critical time and money.

For example, the connector means for obtaining substantially aseptic access between medical components includes (1) spikes or needles that pass through a medical elastomeric diaphragm, which may carry a preformed slit, or which otherwise may be penetrated by the spike cutting through an unslit diaphragm and (2) luer connections in which a tapered, tubular male luer fits into a tapered, tubular female luer socket. Such luer connectors often carry an auxiliary locking feature, and are then typically called a luer lock connector.

Accordingly, in the situation described above, a medical emergency can arise in which a medical set component, for example having a spike, suddenly needs to be connected to a medical component which has a female luer connecter. Since this cannot be accomplished, new, compatible medical components must be brought into play to perform the new medical procedure. That represents a significant disadvantage in medical procedures which require the use of medical sets, syringes, drug vials, sampling containers, and the like.

Also, recent concern has arisen because of the advent of AIDS and other blood-transmissible diseases, in that there is a major need to protect medical personnel from needle sticks as they make and break the many connections between needles and vials, or needles and injection sites on sets, or the like.

In accordance with this invention, a universal connector is provided, which is capable of compatible connection with a wide variety of connection sites, including those sites which utilize an elastomeric diaphragm, as well as female luer-type connection sites. Thus, a medical component which utilizes the connector of this invention is compatible with a wide variety of other medical components to which it may be connected, so that medical procedures can be performed, and quickly varied in their performance when that is needed, without the need to obtain a new set component or the like and to prime it. Because of this, time can be saved which can actually result in the saving of lives, and money can be saved as well.

Additionally, the connector of this invention can be made so that it is very unlikely to accidentally penetrate the skin of the health worker with the consequent risk of disease transmission, so that the universal connector of this invention provides a significant increase in safety over many prior art systems as well as the other advantages.

DESCRIPTION OF THE INVENTION

In this invention, a universal connector is provided, which connector is capable of connection with female luer connectors, as well as connection with resealable-diaphragm connection sites, typically including both preslit diaphragm connection sites and unslit diaphragm connection sites.

The connector of this invention comprises a tubular member defining a first tubular section having a distal end capable of resealably penetrating a latex diaphragm injection site. Aperture means are positioned adjacent the distal end of the tubular section. This first tubular section is typically cylindrical in shape, but it may be of any desirable cross-sectional shape from oval, to square, to triangular, to any irregular cross-sectional shape desired. Also, it may be stepped or tapered. Likewise, the distal end plus the aperture means may be of any known configuration ranging from simply an open ended tube, to a closed, pointed-end tube having side ports, a bevelled-end tube in the manner of a hypodermic needle, a double bevelled end tube, a trocar ended tube, or any other desired tube ending capable of penetrating a latex diaphragm injection site in such a manner that the injection site can reseal upon withdrawal of the needle. Some special end shapes may be provided which are effective only with a preslit latex diaphragm site. Preferably, an end is provided to the first tubular section which is also capable of resealably penetrating an unslit injection site, so that the universal connector is compatible with a wider range of mating connectors.

The first tubular section preferably has a length of about 5 to 16 millimeters. By this, for reasons stated below, the universal connector can be compatible with the typical commercially available female luer connectors. This is so because essentially all commercially available female luer connectors in the medical field comply with the requirements of the American National Standard Institute/Health Industry Manufacturers Association Standards (ANSI standards) Thus, the range of shapes of female luer connectors carried on commercially available medical apparatus is relatively limited in certain ways. Accordingly, it becomes possible to provide a universal connector, when the first tubular section has the length of 5 to 16 millimeters as described above, which can be sealingly compatible not only with essentially all of the resealable-diaphragm connection sites available, but also with the great majority of commercially available female luer connectors in the medical field.

The tubular member of this invention also defines a frustoconical male luer section positioned proximally of the first tubular section described above. This male luer section is proportioned to be sealable with female luer connectors, preferably those female luer connectors that meet the ANSI standards, having a six percent frustoconical taper and other dimensions that fall within a well known range.

The male luer section of the tubular member of this invention has a minimum diameter that is greater than the maximum diameter of the first tubular section described above. Annular step means separates the first tubular section and the male luer section, which step means typically serves as a stop means to limit the penetration of the first tubular section through a diaphragm injection site. Also, means may be provided, spaced proximally of the frustoconical male luer section, for providing connection with a fluid conduit. These means typically comprise a female luer section which is of larger minimum inner diameter than, and completely longitudinally spaced from, the frustoconical male luer section.

Such a universal connector can be fully capable of substantially aseptic connection with a wide variety of resealable-diaphragm connection sites, as well as a wide variety of female luer connectors, particularly those meeting the ANSI standards. As such, a medical set or component, a syringe, or any other medical device becomes capable of universal connection with substantially the entire spectrum of medical sets, drug ampules, vacuum connection ampules, and other medical devices having connectors for the transmission of fluid from one device to another. This provides to any medical device a wide range of connection compatibility throughout the universe of other medical devices, which greatly increases the flexibility that the medical worker has in performing desired medical procedures.

The connector of this invention defines a tubular member as described above which is preferably made of a single, integrally molded plastic piece. The plastic used is typically p.v.c., polypropylene, polycarbonate, or any other appropriate plastic material, typically having a Shore D durometer of about 45 to 120.

The annular step means described above preferably comprises an intermediate tubular section having no outer diameter smaller than the outer diameter of the first tubular section, nor greater than the minimum outer diameter of the male luer section. Preferably, the intermediate, tubular section is separated from the luer section by an annular step.

Preferably, the first tubular section is of a substantially constant diameter of no more than 3 millimeters. This facilitates the resealability of diaphragm type access sites that it penetrates. As stated above, while the first tubular section is substantially cylindrical, it may be of any of a variety of cross sections as well.

In correspondence with the ANSI standard, the conical taper of the luer section of this invention is preferably of such an angle as to cause its transverse dimension to be reduced by about a six percent taper (0.06 mm. per mm. of length).

As has been previously discussed, it is desirable for the first tubular section of this invention to be resistant to the penetration of skin, while it remains capable of penetration of latex diaphragm type connectors. To accomplish this, preferably, the distal end of the first tubular section defines a substantial point having a radius of 0.1 to 0.6 mm., and an included angle of 10 to 40 degrees. The included angle is taken between one side of the end of the distal tubular section where it tapers down to a substantial point, compared with the diametrically opposed, corresponding side of the first tubular section. Such a shape is generally capable of penetrating a latex diaphragm, but it is highly resistant to the penetration of skin, so that needle stick accidents can be avoided. Such a needle can penetrate a latex diaphragm connection site when pressed against it with a loading force of typically no more than about 1.8 kilograms, which force is well within the capabilities of nurses and other medical personnel to manually apply. Preferably, the point of the first tubular section of this invention defines a radius ranging from 0.15 mm. to 0.5 mm.

It is also preferred for the first tubular section to reside completely within an imaginary distal extension of the conical surface of the male luer section, to facilitate good, substantially aseptic connection between the male luer section and a female luer.

If desired, the first tubular section may be lubricated with silicone oil or any other desired lubricating means, to facilitate its penetration through elastomeric closures.

If desired, the connector of this invention may be closed with an end cap, the end cap defining a central prong which extends into the bore of at least the first tubular section. Such an end cap can serve a double function: it protects the end of the universal connector until it is desired for use, and, secondly, the extending prong of the end cap can have a relatively sharp end (particularly if the distal end of the tubular member is fairly blunt) to punch a "starter hole" in a resealable-diaphragm connection site, to facilitate the penetration of the universal connector therethrough.

Accordingly, the universal connector of this invention is capable of providing access to virtually every available medical elastomeric closure in the market, while, at the same time, it is highly resistant to the accidental puncturing of skin. Furthermore, the connector of this invention is capable of access to virtually any ANSI standard female luer connector available in the market. Additionally, the connector of this invention can be designed to be compatible for connection with male luers and other tubular connectors, particularly when the intermediate tubular section defines a shoulder capable of frictionally fitting within the distal ends of such tubular connectors.

While the ANSI standard taper for a luer connection is 6 percent, as stated above, it is possible to obtain good luer connections, if desired, under conditions of greater or less tapering than that, up to a substantially cylindrical surface of zero taper. Particularly, a zero or low taper system may be provided in the circumstance where relatively low durometer plastics are used, so that there is good frictional retention between the connecting parts.

DESCRIPTION OF THE DRAWINGS

In the drawings FIG. 1 is an elevational view of one embodiment of universal connector made in accordance with this invention;

FIG. 2 is an enlarged, longitudinal sectional view of the connector of FIG. 1 taken along line 2—2 of FIG. 1;

FIG. 3 is a fragmentary, enlarged, longitudinal sectional view of the distal end of the universal connector of FIGS. 1 and 2, taken along line 3—3 of FIG. 2 and rotated 90 degrees about the longitudinal axis;

FIGS. 4A through C are elevational views, displaying a sectional portion, of other embodiments of the universal connector of this invention;

FIGS. 5A and 5B are enlarged, partially longitudinal sectional views showing how the universal connector of FIGS. and 2 can mate with differing designs of female luer connectors;

FIG. 6 is a longitudinal sectional view showing the connector of FIG. 1 in connected relation with a tubular connector or male luer;

FIG. 7 is a longitudinal sectional view of another design of the universal connector in accordance with this invention, showing an attached end cap;

FIG. 8 is a longitudinal sectional view showing how the end cap of FIG. 7 can be used to puncture a "starter hole" in a diaphragm prior to penetration by the universal connector; and FIG. 9 is a longitudinal sectional view showing the universal connector of this application as an integral attachment to a syringe.

DESCRIPTION OF SPECIFIC EMBODIMENTS

Referring to FIGS. 1 through 3, a universal connector in accordance with this invention is disclosed, being made of a single piece of molded plastic. As shown, universal connector 10 comprises a tubular member 12 which defines first tubular section 14, which is specifically shown to have a length of 9.5 millimeters from distal end 16 to annular shoulder 18. As particularly shown in FIG. 3, distal end 16 of first tubular section 14 is relatively blunt, tapering down to a point which defines an approximately hemispherical surface having a radius of about 0.15 millimeter, when compared with an overall diameter of first tubular section 14 of about 2 millimeters. Accordingly, the end 16 of universal connector lo is unlikely to penetrate the skin in the event it accidentally strikes the hand. Nevertheless, first tubular section 14 is generally capable of penetrating virtually any needle-piercable diaphragm-type connector, whether or not the diaphragm carries a slit through its surface to facilitate penetration.

A pair of opposed apertures 22 are also provided adjacent pointed tip 16 of the first tubular section 14, for communication of lumen 23 with the exterior.

Also, universal connector 10 further defines a frustoconical male luer section 24 defining a conical taper of 6 percent in accordance with ANSI specifications, and being at least 7.5 millimeters long from its distal end 26 to proximal end 28, and having a minimum outer diameter at end of 3.925 mm. to 4.027 mm..

First tubular section 14 is separated from male luer section 24 by intermediate tubular section 30, which may be 1.2 millimeters in length, including the length of step 18 at its distal end and annular step 32 at its proximal end, by which intermediate section 30 is separated from luer section 24. Steps 18 and 32 can serve as stop members to limit the penetration of universal connector 10 through an elastomeric diaphragm, so that the only penetration thereof is substantially by first tubular section 14. The portion of intermediate tubular section 30 which is between steps 18, 32 may be cylindrical or any other desired shape.

It is preferred for the conical, outer surface of male luer section 24 to define an imaginary distal conical surface extension 25 which surrounds but is spaced from first tubular section 14. This assures that long female luer connectors which meet ANSI specifications can be entered by universal connector 10 without first tubular member 14 entering into contact with the walls of the female luer.

The particular universal connector illustrated in FIG. 2 defines an integrally attached sleeve 34 which defines internal screw threads 36 and an open distal end, as shown, which may preferably conform to the ANSI standard. Additionally, universal connector 10 defines a proximal portion, spaced from male luer section 24, which may serve as a female luer 38, to receive the male luer 40 of a syringe in removably sealed manner if desired, or to provide connection with any other desired medical device. Alternatively, member 38 may be cylindrical, and can receive flexible plastic tubing which may be solvent-sealed in place, so that universal connector 10 may be carried on the end of any type of medical fluid flow set, for example arterial or venous sets for hemodialysis, peritoneal dialysis sets, parenteral solution administration sets, blood administration sets, or the like. Also, member 38 may be a male luer fitting, a barbed fitting, a tube fitting for receiving flexible tubing about its outer diameter, or any other desired shape.

Turning to FIGS. 4A through C, different designs of universal connectors are shown in which the flange 34 of FIGS. 1 through 3 for attachment to a female luer lock connector, may be replaced with other conventional connector designs. Apart from that, the connectors of FIGS. 4A through C may be identical to the connector of FIGS. 1 through 3.

In FIG. 4A, the retention device 34a is analogous in its function to threaded retention sleeve 34 of the previous embodiment, but it comprises a pair of arms which enter into snap-fit relation with a flange or the like of a female luer lock connector, in the manner of certain known connectors.

FIG. 4B discloses a locking member 34b which may be of a conventional bayonet-receiving type, so that a female luer lock connector having a laterally projecting stud ma be rotatably locked into place.

The connector of FIG. 4C carries a loosely mounted threaded sleeve 34c, which is similar to the design of FIGS. 1-3 except for the loose, freely rotatable mounting of the sleeve, for conventional connection with a female luer lock connector.

These various modes of connection 34a-c are all per se well-known, and serve to illustrate that any connector lock mode desired may be used in conjunction with the universal connector of this invention for locking to a female luer lock connector or, if desired, to a piercable diaphragm type connector.

Referring to FIGS. 5A and 5B, the broad tolerance of a connector of this invention in connecting with various designs of female luers is illustrated. As previously described, connector 10 can penetrate a wide variety of resealable-diaphragm connection sites by means of its first tubular section 14 which is proportioned to penetrate virtually any resealable diaphragm of the type used in the medical field. However, when, instead, there is a need to make connection with a female luer, the same connector 10 is shown to be capable of entering into good, sealing connection with female luer 42a in FIG. 5a and 42b in FIG. 5b. In each case, threaded sleeve 34 of luer connector 10 can enter into locking relation with the luer lock hubs 44 of the respective female luers 42a, 42b.

In the circumstance of FIG. 5a, female luer 42a, as shown, is made to the 6% frustoconical minimum permitted length by the ANSI specifications of 7.5 millimeters. No maximum length is defined by the ANSI specifications, as long as it tapers at 6 percent. In that circumstance, the tip 16 of first tubular section 14 penetrates beyond the tapered portion of luer 42a. However, because of the reduced diameter of about 3 millimeters of first tubular section 14, tip 16 can adequately penetrate into the tubular portion 43a of the connector portion 45 that is distal to luer 42a with at least a slight spacing from the walls of portion 45.

On the other hand, as shown in FIG. 5B, a typical length of a commercially available luer as shown is about 14 millimeters. In this circumstance, tip 16 does not penetrate substantially past the narrow end of the tapered luer portion 42b, but, nevertheless, because of the narrow diameter of first tubular section 14, it is capable of occupying without contact of any of the luer walls the interior of luer 42b, to permit good luer sealing connection at area 46 and locking between locking sleeve 34 and lugs 44.

Thus, it can be seen that universal connector 10 is not only capable of penetrating a large variety of resealable-diaphragm connection sites, but it is also capable of mating with essentially all luers that comply with the commercial ANSI specifications in the U.S. and International markets. Thus, the connector of this invention is widely capable of connection with the entire range of such medical devices that are currently available.

Referring to FIG. 6, universal connector 10 is shown to be in connection with a third type of connector, namely a tubular or male luer connector 48. This can be accomplished by making use of the cylindrical portion of intermediate tubular section 30, which is proportioned to mate with a substantial number of tubular male connectors by fitting within the inner diameter of the bore thereof. Since the respective parts are typically made of semirigid plastic, universal connector 10 is capable of frictionally fitting with devices having a certain range of inner diameters at their distal ends 50.

Referring to FIGS. 7 and 8, another embodiment of the universal connector 52 is disclosed. As before, a first tubular section 54 is provided, but in this case tubular section 54 has an open, somewhat blunt distal end 56, typically with the wall thickness tapering down to a fairly narrow annular ring at end 56. First tubular section 54 is separated by annular step means 58 from a frustoconical male luer section 60 which, as before, is proportioned to be sealable with female luer connectors, preferably those conforming to ANSI standards.

Spaced proximally from the frustoconical male luer section 60 is a tubular section 62 for providing connection with a fluid conduit. As before, tubular section 62 may be a female luer, or, alternatively, it may be a male luer fitting, a barbed fitting, a tube fitting, or any other desired shape.

Threaded sleeve 64 is also provided for locking with a female luer lock connector as in the previous embodiment.

This embodiment of FIG. 7 lacks a puncturing point similar to pointed end 16 in the previous embodiment. Accordingly, while first tubular section 54 may be capable of penetrating a slit diaphragm, it may require assistance for penetrating an unslit diaphragm. This may be provided in the form of sealing cap 66 which provides the initial function of sealing the distal end of connector 52. However, when sealing cap 66 is removed, pointed plastic prong 68 is exposed. Accordingly, as shown in FIG. 8, sealing cap 66, after it is removed, may be used to drive the pointed end of prong 68 through a resealable diaphragm connector 69 of a drug vial 70 or the like. After that puncture has been made, first tubular section 54 of universal connector 52 may be more easily advanced through the diaphragm 69 to provide desired communication with drug vial 70.

Then, after the drug has been taken up, or what ever function has taken place with vial 70, the same connector 52 may be removed from drug vial 70 and connected with a female luer of a solution administration set or any other desired medical device, so that the same connector 52 may be used to penetrate the diaphragm and then to link with a luer connection.

Referring to FIG. 9, a conventional syringe 72 for medical solution administration is disclosed, as modified in accordance with this invention. Syringe 72 defines an integral tubular port section 74, which port section constitutes the tubular member in accordance with this invention, comprising a first tubular section 76 and a frustoconical male luer section 77, as shown. Also, syringe 72 carries an internally threaded sleeve 78 so that the system can reliably interlock with a female luer lock connector.

Thus, the syringe can be used to dispense or withdraw medication from a vial, and then it can be transferred and placed into locked relation with a female luer-lock site on a medical set of any type, for the convenient transfer of medication from one medical device to another. For example, such a syringe may be used to collect heparin, and then to administer it to blood via a dialysis set.

The above has been offered for illustrative purposes only, and is not intended to limit the scope of the invention of this application, which is as defined in the claims below.

That which is claimed is:

1. A universal connector made of a single, integrally molded plastic piece, which is capable of both connection with female luer connectors and penetration of resealable-diaphragm connection sites, which connector comprises: a tubular member defining a first tubular section having a distal end capable of resealably penetrating a latex resealable diaphragm injection site, and aperture means adjacent said distal end; said tubular member also defining a frustoconical male luer section positioned proximally of said first tubular section and proportioned to be sealable with female luer connectors, said male luer section having a minimum diameter that is greater than the maximum diameter of said first tubular section; and means, spaced proximally of said frustoconical male luer section, for providing connection with a fluid conduit.

2. The connector of claim 1 in which said first tubular section has a length of about 5 to 16 mm. (said tubular member is made of a single, integrally molded plastic piece).

3. The connector of claim 1 comprising annular step means separating said first tubular section and male luer section, in which said annular step means comprises an intermediate cylindrical section having no outer diameter smaller than that of the first tubular section nor greater than the minimum diameter of the male luer section, said intermediate, cylindrical section being separated from said luer section by an annular step.

4. The connector of claim 1 in which said first tubular section is substantially cylindrical.

5. The connector of claim 1 in which said first tubular section is of a substantially constant diameter of no more than about 3 mm..

6. The connecter of claim 1 which carries means for locking said luer section to a mating female luer connector in connecting relationship.

7. The connector of claim 1 carried on an end of a tubular medical fluid administration device to provide flow connection capability to said device.

8. The connector of claim 1 in which the conical taper of said luer section is of such angle a to cause its transverse dimension to be reduced by about a 6 percent taper (0.06 mm. per mm. of length).

9. The connector of claim 1 in which said distal end of the first tubular section defines a point having a radius of about 0.1 to 0.6 mm. and an included angle of 10° to 40°.

10. The connector of claim 1 in which said distal end of said tubular member defines a pointed end.

11. The connector of claim 1 in which said first tubular section resides completely within an imaginary distal extension of the conical surface of said male luer section.

12. The connector of claim 1 in which said connection providing means spaced proximally of the male luer section defines a female luer for connection with a male luer carried by a tubular medical fluid administration device.

13. The connector of claim 1 in which male luer section defines a minimum outer diameter of essentially 3.925 mm. to 4.027 mm.

14. A syringe which comprises a projecting fluid administration tip, said tip defining an integrally attached connector in accordance with claim 1.

15. The connector of claim 1 in which said first tubular section defines a blunt, open end.

16. The connector of claim 1 which carries cylindrical means for locking to a mating female luer connector in connecting relation, and an end cap engaging the distal end of said cylindrical means and enclosing said first tubular section, said first tubular section defining a distally facing aperture, said end cap defining a prong penetrating said aperture and entering said first tubular section, said prong defining a pointed end.

17. A universal connector which is capable of both connection with female luer connectors and penetration of resealable-diaphragm connection sites, which connector comprises:
a tubular member defining a first tubular section having a distal end capable of resealably penetrating a latex resealable-diaphragm injection site, said distal end of the first tubular section defining a point having a radius of about 0.1 mm. to 0.6 mm.. and aperture means adjacent said distal end, said tubular section also defining a frustoconical male luer section positioned proximally of said first tubular section and proportioned to be sealable with female luer connectors, said male luer section having a minimum diameter that is greater than the maximum diameter of said first tubular section, annular step means separating said first tubular section and male luer section; means, spaced proximally of said frustoconical male luer section, for providing connection with a fluid conduit; and means for locking said luer section to a mating female luer connector in connecting relationship.

18. The connector of claim 17 in which said point defines an included angle of 10° to 40°.

19. The connector of claim 18 in which said tubular member is made of a single, integrally molded plastic piece.

20. The connector of claim 19 in which said annular step means comprises an intermediate cylindrical section having no outer diameter smaller than that of the first tubular section nor greater than the minimum diameter of the male luer section, said intermediate section being separated from said luer section by an annular step.

21. The connector of claim 20 in which said first tubular section is substantially cylindrical of a substantially constant diameter of no more than about 3 mm.

22. The connector of claim 21 in which said first tubular section resides completely within an imaginary distal extension of the conical surface of said male luer section.

23. A universal connector which is capable of both connection with female luer connectors and penetration of resealable-diaphragm connection sites, which connector comprises: a tubular member defining a first tubular section having a distal end capable of resealably penetrating a latex resealable-diaphragm injection site, and aperture means adjacent said distal end; said tubular member also defining a frustoconical male luer section positioned proximally of said first tubular section and proportioned to be sealable with female luer connectors, said male luer section having a minimum diameter that is greater than the maximum diameter of said first tubular section; annular step means separating said first tubular section and male luer section, said annular step means comprising an intermediate cylindrical section having no outer diameter smaller than that of the first tubular section nor greater than the minimum diameter of the male luer section, said intermediate cylindrical section being separated from the male luer section by an annular step substantially perpendicular to the axis of said tubular member; means spaced proximally of said frustoconical male luer section for providing connection with a fluid conduit; and means for locking said luer section to a mating female luer connector in connecting relationship.

24. The connector of claim 23 in which the distal end of the first tubular section defines a point having a radius of about 0.1 mm. to 0.6 mm.

25. The connector of claim 24 in which said first tubular section is substantially cylindrical and of substantially constant diameter of no more than about 3 mm.

26. The connector of claim 25 in which said first tubular section resides completely within an imaginary distal extension of the conical surface of said male luer section.

27. The connector of claim 26 in which said tubular member is made of a single, integrally molded plastic piece.

* * * * *